(12) United States Patent
Bissery

(10) Patent No.: US 6,548,488 B2
(45) Date of Patent: Apr. 15, 2003

(54) COMPOSITION COMPRISING CAMPTOTHECIN OR A CAMPTOTHECIN DERIVATIVE AND AN ALKYLATING AGENT FOR THE TREATMENT OF CANCER

(75) Inventor: Marie-Christine Bissery, Vitry sur Seine (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/799,615

(22) Filed: Mar. 7, 2001

(65) Prior Publication Data

US 2001/0056082 A1 Dec. 27, 2001

Related U.S. Application Data

(60) Provisional application No. 60/190,007, filed on Mar. 17, 2000.

(51) Int. Cl.$^7$ .......................... A61K 31/66; A61K 31/44
(52) U.S. Cl. ....................................... 514/105; 514/283
(58) Field of Search .................................. 514/283, 105

(56) References Cited

U.S. PATENT DOCUMENTS

| | | | |
|---|---|---|---|
| 4,473,692 A | | 9/1984 | Miyasaka et al. |
| 4,545,880 A | | 10/1985 | Miyasaka et al. |
| 5,786,344 A | * | 7/1998 | Ratain et al. ............... 514/100 |
| 6,191,119 B1 | | 2/2001 | Rubinfeld |

FOREIGN PATENT DOCUMENTS

| | | |
|---|---|---|
| EP | 0 056 692 B1 | 7/1982 |
| EP | 0 074256 B1 | 3/1983 |
| EP | 0 088 642 A2 | 9/1983 |
| EP | 0 296 612 B1 | 12/1988 |
| EP | 0 321 122 B1 | 6/1989 |
| EP | 0 325 247 B1 | 7/1989 |
| EP | 0 540 099 B1 | 5/1993 |
| EP | 0 737 686 B1 | 10/1996 |
| WO | WO 90/03169 | 4/1990 |
| WO | WO 96/37496 | 11/1996 |
| WO | WO 96/38146 | 12/1996 |
| WO | WO 96/38449 | 12/1996 |

OTHER PUBLICATIONS

Coggins et al., Cancer Chemother. Pharmacol., (1998), 41(6), 485–490 Abstract Only.*

T.H. Corbett et al., "Evaluation of Single Agents and Combinations of Chemotherapeutic Agents in Mouse Colon Carcinomas," *Cancer*, 40(5):2660–2680 (1977).

T.H. Corbett et al., "Response of Transplantable Tumors of Mice to Anthracenedione Derivatives Alone and in Combination with Clinically Useful Agents," *Cancer Treatment Reports*, 66(5):1187–1200 (May 1982).

David L. Emerson et al., "*In vivo* Antitumor Activity of Two New Seven–substituted Water–soluble Camptothecin Analogues," *Cancer Research*, 55:603–609 (Feb. 1995).

Isabelle Madelaine et al., "Sequential Modifications of Topoisomerase I Activity in a Camptothecin–Resistant Cell Line Established by Progressive Adaptation," *Biochemical Pharmacology*, 45(2):339–348 (1993).

Tomio Furuta and Teruo Yokokura, "Combination Therapy of CPT–11, a Camptothecin Derivative, with Various Antitumor Drugs Against L1210 Luekemia," *Japanese Journal of Cancer and Chemotherapy*, 18(3):393–402 (Mar. 1991); English Absrtact p. 402.

Abstract Japio No. 00965715 for JP 57–116015.

Abstract Japio No. 00965774 for JP 57–116074.

Abstract Japio No. 01293588 for JP 59–5188.

Abstract Japio No. 01541290 for JP 60–19790.

Abstract Japio No. 02948687 for JP 1–246287.

Abstract Japio No. 02952177 for JP 1–249777.

Abstract: Derwent No. 01984–110813/198418 for JP 59–051289.

Frank M. Schabel, Jr. et al., "Testing Therapeutic Hypotheses in Mice and Man: Observations on the Therapeutic Activity Against Advanced Solid Tumors of Mice Treated with Anticancer Drugs That Have Demonstrated or Potential Clinical Utility for Treatment of Advanced Solid Tumor of Man," *Methods of Cancer Research*, 17(Part)B:3–51 (1979).

P. Vrignaud et al., "*In vivo* chemosensitivity of a P388 murine leukemia resistant to camptothecin," *Proceedings of the Americant Association for Cancer Research*, 35:363 (Mar. 1994), Abstract.

* cited by examiner

*Primary Examiner*—Jerome D. Goldberg
(74) *Attorney, Agent, or Firm*—Finnegan, Henderson, Farabow, Garrett & Dunner LLP

(57) ABSTRACT

The present invention relates to therapeutic associations for the treatment of cancer, comprising an effective amount of a camptothecin, or a camptothecin derivative, with an effective amount of an alkylating agent, such as melphalan, dacarbazine, or cyclophosphamide, and methods of using such therapeutic associations.

8 Claims, 2 Drawing Sheets

EVALUATION OF CPT-11 IN COMBINATION WITH CYCLOPHOSPHAMIDE AGAINST
MAMMARY ADENOCARCINOMA MA16/C/sp ON C3H/HeN FEMALE MICE

BCM-929 (03.14.97-04.18.97)

| AGENT (BATCH) | ROUTE | DOSAGE IN MG/KG/DOSE | SCHEDULE IN DAYS | TOTAL DOSE IN MG/KG | FRACTION OF HNTD | DRUG DEATH (DAYS OF DEATH) | AVERAGE BODY WEIGHT CHANGE IN % PER MOUSE AT NADIR (DAY OF NADIR) |
|---|---|---|---|---|---|---|---|
| CPT-11 | P.O. 0.2 ml | 103.0 | 3 TO 7 | 515 | | 5/5 (10, 3D11, 12) | -29.4 (10) |
| | | 64.0 | | 320 | | 0/5 | -19.6 (10) |
| | | 40.0 | | 200 | 1 | 0/5 | -6.9 (9) |
| | | 25.0 | | 125 | | 0/5 | -2.9 (6) |
| CPA | I.V. 0.2 ml | 156.0 | 3,5,7 | 468 | | 4/5 (10, 2D11, 29) | - |
| | | 97.0 | | 291 | 1 | 0/5 | -7.1 (9) |
| | | 60.0 | | 180 | | 0/5 | -5.8 (8) |
| | | 37.0 | | 111 | | 0/5 | -4.6 (9) |
| | | 23.0 | | 69 | | 0/5 | -1.7 (4) |
| CPT-11 | P.O. 0.2 ml | 64.0 | 3 - 7 | 320 | 1.60) | | |
| CPA | I.V. 0.2 ml | 60.0 | 3,5,7 | 180 | 0.62) 2.2 | 1/5 (9) | -20.1 (10) |
| | | 57.6 | | 288 | 1.44) | | |
| | | 54.0 | | 162 | 0.56) 2.0 | 0/5 | -14.4 (9) |
| | | 48.0 | 3 TO 7 | 240 | 1.20) | | |
| | | 45.0 | 3,5,7 | 135 | 0.46) 1.66 | 0/5 | -9.2 (9) |
| | | 38.4 | 3 TO 7 | 192 | 0.96) | | |
| | | 36.0 | 3,5,7 | 108 | 0.37) 1.33 | 0/5 | -3.2 (9) |
| | | 28.8 | 3 TO 7 | 144 | 0.72) | | |
| | | 27.0 | 3,5,7 | 81 | 0.28) 1.00 | 0/5 | -1.1 (7) |
| | | 19.2 | 3 TO 7 | 96 | 0.48) | | |
| | | 18.0 | 3,5,7 | 54 | 0.19) 0.67 | 0/5 | -0.9 (5) |
| | | 51.2 | 3 TO 7 | 256 | 1.28) | | |
| | | 24.0 | 3,5,7 | 72 | 0.25) 1.53 | 0/5 | -9.9 (9) |
| | | 25.6 | 3 TO 7 | 128 | 0.64) | | |
| | | 48.0 | 3,5,7 | 144 | 0.49) 1.13 | 0/5 | -4.9 (10) |
| CONTROL | | | | | | | |

TUMOR DOUBLING TIME = 1.1 DAYS
MICE AVERAGE WEIGHT: CPT-11 = 20.83 g, CYCLOPHOSPHAMIDE (CPA) = 22.22 g AND 21.98 g FOR NTBA, COMBINATION = 21.34 g AND 21.10 g FOR NTBA.

FIG. 1A

EVALUATION OF CPT-11 IN COMBINATION WITH CYCLOPHOSPHAMIDE AGAINST MAMMARY ADENOCARCINOMA MA16/C/SP ON C3H/HeN FEMALE MICE

BCM-929 (03.14.97-04.18.97)

| AGENT (BATCH) | MEDIAN TUMOR WEIGHT IN MG ON DAY 9 (RANGE) | T/C IN % ON DAY 9 | TIME FOR MEDIAN TUMOR TO REACH 750 MG IN DAYS | T-C IN DAYS | LOG CELL KILL TOTAL | TUMOR FREE SURVIVORS DAY 21 | COMMENTS |
|---|---|---|---|---|---|---|---|
| CPT-11 | - | - | - | - | - | 0/5 | TOXIC |
| | - | - | - | - | - | 0/5 | TOXIC 20% BWL |
| | 0 (0-32) | 0 | 15.5 | 7.3 | 2.0 | 0/5 | HNTD ACTIVE |
| | 56 (32-73) | 5 | 12.3 | 4.1 | 1.1 | 0/5 | ACTIVE |
| CPA | NTBA | NTBA | NTBA | NTBA | NTBA | NTBA | TOXIC[a] |
| | 0 (0-23) | 0 | 18.5 | 10.3 | 2.8 | 0/5 | HNTD HIGHLY ACTIVE |
| | 18 (0-48) | 2 | 15.1 | 6.9 | 1.9 | 0/5 | ACTIVE |
| | 139 (123-380) | 13 | 12.0 | 3.8 | 1.0 | 0/5 | ACTIVE[b] |
| | 543 (188-690) | 49 | - | - | - | 0/5 | INACTIVE |
| CPT-11 CPA | NTBA | NTBA | NTBA | NTBA | NTBA | NTBA | TOXIC |
| | 0 (0-0) | 0 | 21.1 | 12.9 | 3.5 | 0/5 | HNTD HIGHLY ACTIVE |
| | 0 (0-18) | 0 | 18.9 | 10.7 | 2.9 | 0/5 | HIGHLY ACTIVE |
| | 0 (0-0) | 0 | 18.4 | 10.2 | 2.8 | 0/5 | HIGHLY ACTIVE |
| | 0 (0-0) | 0 | 15.4 | 7.2 | 2.0 | 0/5 | ACTIVE |
| | 0 (0-0) | 0 | 12.9 | 4.7 | 1.3 | 0/5 | ACTIVE |
| | 0 (0-0) | 0 | 18.2 | 10.0 | 2.7 | 0/5 | ACTIVE |
| | 0 (0-0) | 0 | 18.9 | 10.7 | 2.9 | 0/5 | HIGHLY ACTIVE |
| CONTROL | 1099 (306-1844) | | 8.2 | | | 0/10 | |

[a] NON TUMOR-BEARING ANIMALS FROM ANOTHER BATCH OF MICE.
[b] ONE TUMORAL DEATH ON DAY 14
ABBREVIATIONS USED: BWL = BODY WEIGHT LOSS,
HNTD = HIGHEST NONTOXIC DOSE, NTBA = NON TUMOR-BEARING ANIMALS.

*FIG. 1B*

COMPOSITION COMPRISING CAMPTOTHECIN OR A CAMPTOTHECIN DERIVATIVE AND AN ALKYLATING AGENT FOR THE TREATMENT OF CANCER

The present application claims the benefit of U.S. Provisional Application No. 60/190,007, filed Mar. 17, 2000.

The present invention relates to therapeutic combinations comprising an effective amount of camptothecin, or a camptothecin derivative such as irinotecan (CPT-11), with an effective amount of an alkylating agent for the treatment of cancer.

More specifically, the invention relates to anticancer treatments with associations of camptothecin derivatives such as irinotecan (CPT-11, CAMPTOSAR®), topotecan, 9-aminocamptothecin, or 9-nitrocamptothecin, and alkylating agents. Such alkylating agents include, inter alia, melphalan (alkeran, L-3-{para-[Bis(2-chloroethyl)amino]phenyl}alanine, CB 3025, phenylalanine mustard, L-Sarcolysine, SK-15673), dacarbazine (DTIC-Dome®, DTIC, dimethyl triazeno imidazole carboxamide; 5-(3,3-dimethyl-1-triazenyl)-1H-imidazole-4-carboxamide, 9CI, DIC), and cyclophosphamide (CPA, CYTOXAN®, NEOSAR®).

European patent EP 137,145, specifically incorporated by reference herein, describes camptothecin derivatives of the formula:

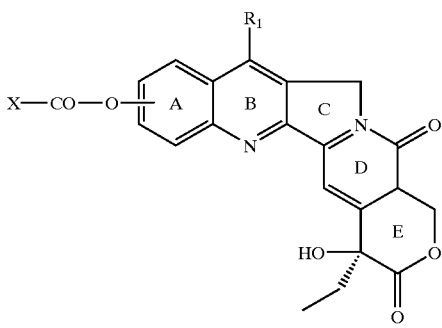

in which, in particular, $R_1$ is hydrogen, halogen or alkyl; X is a chlorine atom, or $NR_2R_3$, in which $R_2$ and $R_3$, which may be identical or different, may represent a hydrogen atom, an optionally substituted alkyl radical, a carbocycle or a heterocycle which are optionally substituted, or alkyl radicals (optionally substituted) forming, with the nitrogen atom to which they are attached, a heterocycle optionally containing another heteroatom chosen from O, S, and/or $NR_4$, wherein $R_4$ is a hydrogen atom or an alkyl radical; and in which the group X—CO—O— is located on ring A in position 9, 10, or 11.

These camptothecin derivatives are anticancer agents which inhibit topoisomerase I, among which irinotecan, in which X—CO—O— is [4-(1-piperidino-1-piperidino] carbonyloxy, is an active principle which is particularly effective in treatment of solid tumors. Camptothecin and camptothecin derivatives such as irinotecan are cytotoxic alkaloids which possesses strong anti-tumor activities. Irinotecan shows clinical activity against colon, gastric, ovarian, and small cell lung cancers, as well as non-Hodgkin's lymphoma (Bissery, M. et al., *Anti Cancer Drugs*, 7:166–174 (1996)).

The European patent application EP 74,256 also describes other camptothecin derivatives which are also mentioned as anticancer agents, in particular, derivatives of a structure analogous to the structure given above and in which X—CO—O— is replaced with a radical —X'R' for which X' is O or S, and R' is a hydrogen atom or an alkyl or acyl radical.

Other camptothecin derivatives have also been described, for example, in the following publications, patents, or patent applications: EP 56,692; EP 88,642; EP 296,612; EP 321,122; EP 325,247; EP 540,099; EP 737,686; WO 90/03169; WO 96/37496; WO 96/38146; WO 96/38449; WO 97/00876; U.S. Pat. No. 7,104,894; JP 57 116,015; JP 57 116,074; JP 59 005,188; JP 60 019,790; JP 01 249,777; JP 01 246,287; and JP 91 12070; *Canc. Res.*, 38 (1997) Abstr. 1526 or 95 (San Diego, April 12–16); *Canc. Res.*, 55(3):603–609 (1995); or *AFMC Int. Med. Chem. Symp.* (1997) Abstr. PB-55 (Seoul, Korea; July 27–August 1).

Camptothecin derivatives are usually administered by injection, more particularly intravenously in the form of a sterile solution or an emulsion. Camptothecin derivatives, however, can also be administered orally, in the form of solid or liquid compositions.

However, while camptothecin and camptothecin derivatives are considered to be some of the most powerful substances possessing anti-tumor activity, for example in colorectal cancers, the use of these compounds can be improved by association with other antitumor agents.

Among such antitumor agents are alkylating agents which have antineoplastic activity. Such alkylating agents include inter alia melphalan (alkeran, L-3-{para-[Bis(2-chloroethyl)amino]phenyl}alanine, CB 3025, phenylalanine mustard, L-Sarcolysine, SK-15673), dacarbazine (DTIC-Dome®, DTIC, dimethyl triazeno imidazole carboxamide; 5-(3,3-dimethyl-1-triazenyl)-1H-imidazole-4-carboxamide, 9CI, DIC), and cyclophosphamide (CPA, CYTOXAN®, NEOSAR®).

It has been discovered that combinations of camptothecin and an alkylating agent such as cyclophosphamide significantly reduce the development of tumor volume compared to the development of tumor volume from the administration of each compound alone, as predicted from administration to tumor-infected mammals.

The combination of CPT-11 and cyclophosphamide has been studied in Japan (Furuta, Tomio et al., *Cancer Chemotherapy*, 18(3): 393–402 (1991)). In that study, however, the evaluation of the combination was only conducted on L1210 mouse leukemia, not on solid tumors. The route of administration of CPT-11 and cyclophosphamide was via the abdominal cavity, that is, the drugs were administered intraperitoneally and not orally or intravenously. Furthermore, Furuta et al. did not evaluate the effect of the highest non-toxic dose of either camptothecin or cyclophosphamide as single agents. Without such a determination, it is not possible to determine the synergistic effect of the CPT-11/cyclophosphamide combination.

It has now been found that the combination of CPT-11 and cyclophosphamide is more active at a lower dose than the highest non-toxic dose of each single agent for the treatment of cancer, including, for example, mammary adenocarcinoma. PATENT The efficacy of a combination may be demonstrated by determination of therapeutic synergy. A combination manifests therapeutic synergy if it is therapeutically superior to one or other of the constituents used at its optimum dose (T. H. Corbett et al., *Cancer Treatment Reports*, 66: 1187 (1982)).

The efficacy of a combination may also been demonstrated by comparison of the maximum tolerated dose of the combination with the maximum tolerated dose of each of the separate constituents in the study in question. This efficacy may be quantified, for example by the $\log_{10}$ cell kill, which is determined by the following formula:

$$\log_{10} \text{ cell kill} = T\text{-}C(\text{days})/3.32 \times T_d$$

in which T-C represents the time taken for the cells to grow, which is the mean time in days for the tumors of the treated group (T) to reach a predetermined value (1 g for example) and the tumors of the control group (C) to reach the same value, and $T_d$ represents the time in days needed for the volume of the tumor in the control group to double (T. H. Corbett et al., *Cancer*, 40: 2660–2680 (1977); F. M. Schabel et al., *Cancer Drug Development, Part B, Methods in Cancer Research*, 17: 3–51, New York, Academic Press Inc. (1979)). A product is considered to be active if the $\log_{10}$ cell kill is greater than or equal to 0.7. A product is considered to be very active if the $\log_{10}$ cell kill is greater than 2.8.

It has now been found that administration of CPT-11 in combination with cyclophosphamide in the following manner with the following schedules results in a combination that is very active against cancers. Furthermore, the combination of CPT-11/cyclophosphamide is more active at a lower dose than the highest non-toxic dose of either CPT-11 or cyclophosphamide alone.

The products may be administered simultaneously, semi-simultaneously, separately, or spaced out over a period of time so as to obtain the maximum efficacy of the combination. As a result, the invention is not limited to the compositions obtained by the physical association of the drugs, but also includes those which permit separate administration, either simultaneously, semi-simultaneously, or spaced out over a period of time.

BRIEF DESCRIPTION OF THE DRAWING

FIG. 1 presents a table evaluating irinotecan (CPT-11), cyclophosphamide, and the combination thereof as therapeutics against mammary adenocarcinoma in a murine model system.

EXAMPLE 1

The effect of the combination of CPT-11 and cyclophosphamide was evaluated in a three arn study in mice bearing mammary adenocarcinoma MA16/C/sp. In the first arm, four dose levels of CPT-11 were given orally on days three through seven. In the second arm, five dose levels of cyclophosphamide were given intravenously on days three, five and seven. In the combination third arm, eight dosage levels of CPT-11 were administered orally on days three through seven, with administration of eight dosage levels of cyclophosphamide intravenously on days three, five and seven. This third arm illustrated an example of semi-simultaneous administration. The results obtained in the study of single agents CPT-11 and cyclophosphamide and the combination CPT-11/cyclophosphamide are given below in Table I.

TABLE I

Evaluation of CPT-11 in Combination with Cyclophosphamide (CPA)
Against Mammary Adenocarcinoma MA/C/sp on C3H/HeN Female Mice CM-929

| Agent | Route | Dosage (mg/kg/adm) | Schedule (days) | $\log_{10}$ cell kill | T-C (days) | Time for median tumor to reach 750 mg in days | Comments |
|---|---|---|---|---|---|---|---|
| CPT-11 | p.o., 0.2 ml | 103.0 | 3–7 | — | — | — | Toxic |
| CPT-11 | p.o., 0.2 ml | 64.0 | 3–7 | — | — | — | Toxic |
| CPT-11 | p.o., 0.2 ml | 40.0 | 3–7 | 2.0 | 7.3 | 15.5 | HNTD Active |
| CPT-11 | p.o., 0.2 ml | 25.0 | 3–7 | 1.1 | 4.1 | 12.3 | Active |
| CPA | i.v., 0.2 ml | 156.0 | 3, 5, 7 | NTBA | NTBA | NTBA | Toxic |
| CPA | i.v., 0.2 ml | 97.0 | 3, 5, 7 | 2.8 | 10.3 | 18.5 | HNTD Highly Active |
| CPA | i.v., 0.2 ml | 60.0 | 3, 5, 7 | 1.9 | 6.9 | 15.1 | Active |
| CPA | i.v., 0.2 ml | 37.0 | 3, 5, 7 | 1.0 | 3.8 | 12.0 | Active |
| CPA | i.v., 0.2 ml | 23.0 | 3, 5, 7 | — | — | — | Inactive |
| CPT-11 + | p.o., 0.2 ml | 64.0 | 3–7 | NTBA | NTBA | NTBA | Toxic |
| CPA | i.v., 0.2 ml | 60.0 | 3, 5, 7 | | | | |
| CPT-11 + | p.o., 0.2 ml | 57.6 | 3–7 | 3.5 | 12.9 | 21.1 | HNTD Highly Active |
| CPA | i.v., 0.2 ml | 54.0 | 3, 5, 7 | | | | |
| CPT-11 + | p.o., 0.2 ml | 48.0 | 3–7 | 2.9 | 10.7 | 18.9 | Highly Active |
| CPA | i.v., 0.2 ml | 45.0 | 3, 5, 7 | | | | |
| CPT-11 + | p.o., 0.2 ml | 38.4 | 3–7 | 2.8 | 10.2 | 18.4 | Highly Active |
| CPA | i.v., 0.2 ml | 36.0 | 3, 5, 7 | | | | |
| CPT-11 + | p.o., 0.2 ml | 28.8 | 3–7 | 2.0 | 7.2 | 15.4 | Active |
| CPA | i.v., 0.2 ml | 27.0 | 3, 5, 7 | | | | |
| CPT-11 + | p.o., 0.2 ml | 19.2 | 3–7 | 1.3 | 4.7 | 12.9 | Active |
| CPA | i.v., 0.2 ml | 18.0 | 3, 5, 7 | | | | |
| CPT-11 + | p.o., 0.2 ml | 51.2 | 3–7 | 2.7 | 10.0 | 18.2 | Active |
| CPA | i.v., 0.2 ml | 24.0 | 3, 5, 7 | | | | |
| CPT-11 + | p.o., 0.2 ml | 25.6 | 3–7 | 2.9 | 10.7 | 18.9 | Highly Active |
| CPA | i.v., 0.2 ml | 48.0 | 3, 5, 7 | | | | |

CPA: cyclophosphamide;
HNTD: highest non-toxic dose;
NTBA: non tumor-bearing animals;
p.o.: per os;
i.v.: intravenous;
T-C: tumor growth delay
The data comprising this table was compiled from FIG. 1.

The combination of cyclophosphamide and irinotecan was therapeutically superior to either of the single agents used at its optimum dose. The CPT-11-cyclophosphamide combination at its highest non toxic dose produced a $\log_{10}$ cell kill of 3.5, while the $\log_{10}$ cell kill of the highest non toxic dose of both CPT-11 and cyclophosphamide as single agents were 2.0 and 2.8, respectively. Therefore, it can be seen that the CPT-11/cyclophosphamide combination was synergistically active and highly active against mammary adenocarcinoma at the highest non-toxic combination dose level, and active or highly active at other combination dose levels. The combination was therefore therapeutically superior to both of the single agents used at its optimum dose. Additionally, the combination showed greater therapeutic activity, in that the time for a median tumor to reach 750 mg in days was longer at the highest non-toxic combination dose level than in either single agent administration of irinotecan or cyclophosphamide at the highest non-toxic dose. Further, the irinotecan/cyclophosphamide combination gave a broader highly active and active dose response than the individual agents.

EXAMPLE 2

The effectiveness of irinotecan combination chemotherapy methods were tested in a dose response study in a murine tumor model. Three arms were evaluated for tolerance and efficacy. Tolerance was measured by mortality, body weight loss at nadir, host recovery time, and combination toxicity index. Efficacy end points for solid tumor models were tumor growth delay (T/C), $\log_{10}$ cell kill (LCK, defined above), tumor regressions (i.e., complete remission (CR),or partial remission (PR)). For non-solid tumors, such as leukemia, efficacy was measured as the increase in life span (ILS).

Combination toxicity index (CTI) was calculated as the sum of the fraction of $LD_{10}$'s for each agent used in each combination (*Cancer Treatment Reports*, 66(5): 1187–1200 (1982)). The $LD_{10}$ for the single agent was obtained by plotting the toxicity of that agent and the dosage in mg/kg as a log probit graph. Subsequently, the CTI $LD_{10}$ was obtained by plotting as a log probit graph the observed lethality and the corresponding CTI calculated as the sum of the fraction of the $LD_{10}$ of each single agent. When the CTI equals one, only 50% of the $LD_{10}$'s of each agent can be used in combination without additional toxicity, and when the CTI equals two, 100% of the $LD_{10}$'s of each agent can be used in combination without additional toxicity.

The optimal total dose for oral and intravenous administration routes for irinotecan alone in various murine models is indicated in Table II.

TABLE II

Comparison of Oral and I.V. Irinotecan Administration

| Tumor (mice) | Route | Schedule days | Optimal Total Dose mg/kg | LCK |
|---|---|---|---|---|
| C51 (BALB/c) | oral | 5, 7, 9, 13, 15, twice daily* | 845 | 2.5 |
| | i.v. | 5, 7, 9, 13, 15, twice daily* | 615 | 3.0 |
| C26 (BALB/c) | oral | 3–7 twice daily* | 558 | 0.9 |
| | i.v. | twice daily* | 228 | 0.7 |
| P03 (B6D2F1) | oral | twice daily* | 900 | 3.4† |
| | i.v. | twice daily* | 346.2 | 3.2† |
| MA16/C (C3H/HeN) | oral | 5–9 | 230.5 | 2.7 |
| | i.v. | 5–9 | 130.5 | 2.6 |
| GOS (B6D2F1) | oral | 3–7, twice daily* | 900 | 2.1 |
| | i.v. | 3, 5, 7 twice daily* | 346.2 | 2.2 |

*The two administrations were 4 hours apart. †1/5 tumor free survivor on day 120.

Both methods of administration resulted in similar tolerance, as measured by body weight loss (8.5%), nadir (7 days post last administration), and recovery (5 days post nadir, i.e., 12 days post first administration). This study showed that the efficacy in tumor bearing mice was similar for oral and i.v. irinotecan administration across all five tumor models tested in three different mice strains. The oral maximum tolerated dose for irinotecan was shown to be about 1.4 to 2.6 times the i.v. maximum tolerated dose.

Cross-resistance was measured in murine leukemia cell lines. P388/CPT is a camptothecin-resistant leukemia that was established in vitro (*Biochem. Pharmacol.*, 45: 339 (1993) and maintained in vivo by i.p. passages in DBA2 female mice. The chemosensitivity of i.p. P388/CPT was evaluated with i.v. P388 sensitive reference drugs with different mechanisms of action. Antitumor efficacy was determined at the highest non-toxic dose as percent increase in life span (ILS), where:

$$ILS = 100 \times [(\text{median day of death (MDD) of treated mice}) - (MDD \text{ control mice})] \div (MDD \text{ control mice})$$

A minimal level of activity equals an ILS of greater than 26%. P388/CPT was found resistant to camptothecin s.c. and CPT-11, but both camptothecin resistant and camptothecin sensitive cell lines were very sensitive to the alkylating agent cyclophosphamide. These results show that this cell line was sensitive to alkylating agents regardless of camptothecin resistance (Vrignaud, P. et al., *Proc. Amer. Assoc. Cancer Res.*, 35: 363, Abstract No. 2163 (1994)). Table III tabulates the results from this study.

TABLE III

| Agents[\] ILS | P388 | P3 88/CPT (TFS) | Comment |
|---|---|---|---|
| CPT (sc) | 82 | 0 | resistant |
| CPT-11 (i.v.) | 91 | 0 | resistant |
| Cyclophosphamide (i.v.) | 245 | 153 (1/5 TS) | sensitive |

The results for irinotecan (CPT-11) administered intravenously and simultaneously with the alkylating agent cyclophosphamide are shown in Table IV.

TABLE IV

| CPT-11 plus: | Tumor site | Schedule | % HNTD of single agents | Host recovery (days) | Therapeutic response |
|---|---|---|---|---|---|
| cyclophosphamide sc | MA 16/C, | simult. | 75 | 11 | ≧ |

HNTD represents the highest nontoxic dose. ≧: Better dose response for the combination.

Table V compares different application methods for the alkylating agent cyclophosphamide alone and in combination, i.e., i.v. or per os (p.o.), as indicated.

TABLE V

| Agents | Tumor site | Schedule days | HNTD Dose mg/kg | LCK | CTI |
|---|---|---|---|---|---|
| CPT-11, i.v. | MA16/C, sc | 3–7 | 200 | — | 2.0 |
| cyclophosphamide, i.v. | | 3, 5, 7 | — | 291 | 2.8 |
| combination | | | 288 | 162 | 3.5 | ≅1.5 |

HNTD represents the highest nontoxic dose.

This study confirmed the positive results obtained in Example 1. Simultaneous administration of irinotecan with cyclophosphamide at only 75% of the highest non-toxic dose was more effective than either agent alone in a mammary adenocarcinoma model system. Cyclophosphamide and irinotecan in combination gave a very active therapeutic profile, and were more active than either agent alone. The CPT-11/cyclophosphamide combination at its highest non toxic dose produced a $\log_{10}$ cell kill of 3.5, while the $\log_{10}$ cell kill of the highest non-toxic dose of both CPT-11 and cyclophosphamide as single agents were 2.0 and 2.8, respectively. Hence, this combination was therapeutically synergistic. The CPT-11/cyclophosphamide combination was well tolerated, with a combination toxicity index of 1.5, indicating that 75% of the highest nontoxic does of the single agent could be combined without additional toxicity.

In conclusion, the combination of an alkylating agent, such as cyclophosphamide, with irinotecan or other camptothecin derivative, is a highly active pharmaceutical composition and represents a new method for treating cancer.

I claim:

1. A method of treating a subject having at least one solid tumor, said method comprising administering to said subject a synergistic combination of CPT-11 and an alkylating agent by orally administering CPT-11 as a first agent, and intravenously administering cyclophosphamide as a second agent, wherein said at least one solid tumor is sensitive to said combination.

2. The method according to claim 1, wherein the agents are administered simultaneously, semi-simultaneously, or separately.

3. The method according to claim 2, wherein said method treats at least a mammary adenocarcinoma.

4. The method according to claim 1, wherein said method treats at least a mammary adenocarcinoma.

5. A method of treating a subject having at least one solid tumor, said method comprising administering to said subject a synergistic combination of CPT-11 and an alkylating agent by intravenously administering CPT-11 as a first agent and cyclophosphamide as a second agent, wherein said at least one solid tumor is sensitive to said combination.

6. The method of claim 5, wherein the agents are administered simultaneously, semi-simultaneously, or separately.

7. The method according to claim 6, wherein said method treats at least a mammary adenocarcinoma.

8. The method according to claim 5, wherein said method treats at least a mammary adenocarcinoma.

* * * * *